United States Patent [19]

Williams

[11] Patent Number: Plant 5,270

[45] Date of Patent: Aug. 14, 1984

[54] MINIATURE ROSE PLANT—WILBENTUR VARIETY

[75] Inventor: J. Benjamin Williams, Silver Spring, Md.

[73] Assignee: The Conard-Pyle Company, West Grove, Pa.

[21] Appl. No.: 393,862

[22] Filed: Jun. 30, 1982

[51] Int. Cl.[3] ..... A01H 5/00

[52] U.S. Cl. ..... Plt./8

[58] Field of Search ..... Plt./8–9

*Primary Examiner*—Robert E. Bagwill

*Attorney, Agent, or Firm*—Burns, Doane, Swecker & Mathis

[57] ABSTRACT

A new and distinct variety of Miniature rose plant is provided having very attractive petite double flowers which are white with a light pink blush. The new variety resulted from the crossing of the Ma Perkins variety (U.S. Plant Pat. No. 1,143) and the Easter Morning variety (U.S. Plant Pat. No. 2,177). This new variety is extremely floriferous during the entire growing season making it particularly well suited for use in parks and gardens. The plant commonly achieves a height of only approximately 8 to 12 inches.

2 Drawing Figures

SUMMARY OF THE INVENTION

The object of the present invention is to provide a new variety of rose plant of the Miniature Class which is disintinguished from prior varieties by the following combination of charateristics:

(a) from the physical standpoint the plant with light green adult wood has a low compact growth habit, and forms clusters of very double white flowers which often have a pink blush toward the center; and (b) from the biological standpoint the plant has vigorous and regular vegetation, and exhibits an abundant and repeated florescence throughout the growing season thereby creating a substantially constant floral display.

The plant commonly achieves a height of only approximately 8 to 12 inches.

In view of these characteristics the new variety meets the needs of the horticultural industry and is particularly suited to ornamental use in garden borders and in beds, The new variety resulted from artificial pollination with the variety Ma Perkins (U.S. Plant Pat. No. 1,143) serving as the seed parent, and the variety Easter Morning (U.S. Plant Pat. No. 2,177) serving as the pollen parent.

The characteristics and properties of this new variety have been found to be transmissible by vegetative propagation, through softwood cuttings, grafting and budding performed at West Grove, Pa.

The rose plant of the new variety has been named the Wilbentur variety. Plants of the new variety presently are being marketed by the Conard-Pyle Co. of West Grove, Pa. under the PIXIE DELIGHT trademark.

BRIEF DESCRIPTION OF THE PHOTOGRAPHS

The accompanying photographs show as nearly true as it is possible to make the same in color illustrations of this character, typical specimens of plant parts from two year old plants produced from softwood cuttings and growing in the open air during mid-June at West Grove, Pa. Since the plants were grown in considerable heat under intense light conditions, a pink blush which would otherwise be present on the blossoms is not visible.

In FIG. 1 is shown a simple floral arrangement showing the blossoms in various stages of opening and foliage of the new variety.

In FIG. 2 are shown various plant parts of the new variety. At the left portion of the photograph are shown clusters of buds and foliage. In the upper center portion of the photograph are shown buds and blossoms in various stages of opening. In the right portion of the photograph is shown a segment of a flowering stem. In the lower center of the photograph are shown leaves of three, five, and seven leaflets.

DETAILED DESCRIPTION

Figure 1:
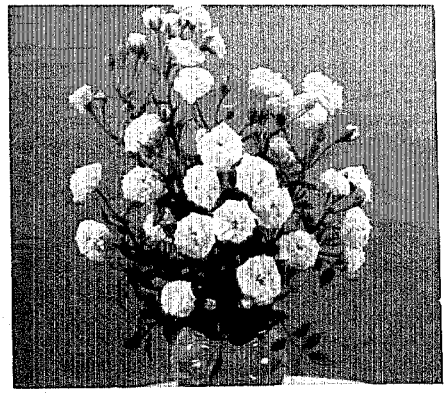
Figure 2:
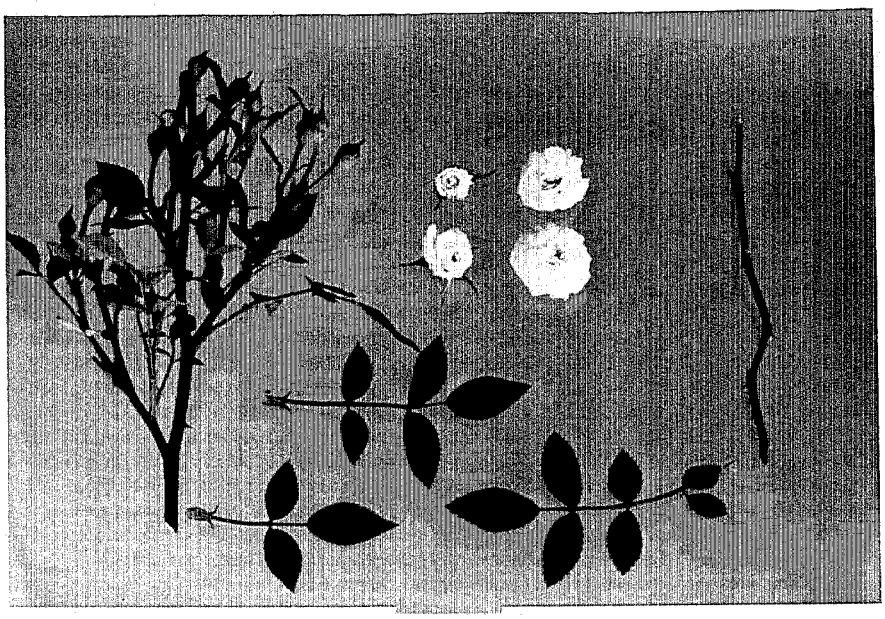

The plants described were grown outdoors at West Grove, Pa., and were observed during the month of June.

The chart utilized in the identification of the colors is that of The Royal Horticultural Society (R.H.S. Colour Chart).

Class: Miniature.

Plant:

*Height.*—Approximately 20 to 30 cm. on average.

*Bearing.*—Low and compact.

Branches:

*Color.*—Young stems: shiny bronzed green, Yellow-Green Group 146B, with cast of Greyed-Orange Group 173A. Mature wood: light green, Yellow-Green Group 144A.

*Thorns.*—Shape of upper edge: slightly concave. Shape of lower edge: straight to concave. Size: medium to small. Quantity: medium. Color: reddish, fading to greenish-red on older wood.

Foliage:

*Stipules.*—Doubly serrate, partially detached, arching approximately 45 degrees away from petiole.

*Petiole.*—Inner surface: grooved, reddish green (young leaves) and medium green with red on edges of grooves (adult leaves), tomentose with prickles along edges. Outer surface: light reddish green (young leaves) and yellow-green (adult leaves), bears moderate to heavy hooked prickles.

*Leaflets.*—Number: 3 occasionally, but more often 5 or 7, approximately 1 to 2 cm. in length on average, approximately 0.6 to 1.3 cm. in width on average. Shape: usually elliptical, but sometimes ovate, with rounded base. Teeth: serrulate. General effect: very abundant, dense, shiny foliage.

*Color.*—Young leaves: Upper surface: dark green, Yellow-Green Group 146A, with red edge. Lower surface: medium green, Yellow-Green Group 148B, with heavy red cast, 178B Greyed-Red Group. Mature leaves: Upper surface: medium-green, Yellow-Green Group 146A. Lower surface: Green Group 138B.

Flowers:

*Number of flowers.*—Commonly 2 to 5 flowers per stem.

*Peduncle.*—Moderate thickness, curving, almost entirely heavy red, Greyed-Red Group 178B, hairy and approximately 2.5 to 3.5 cm. in length on average.

*Sepals.*—Inner surface: tomentose, light green with vague red edge. Outer surface: medium green with red edges and spine.

*Bud.*—Shape: globular, semi-conspicuous neck. Size: very petite, approximately 0.5 to 0.7 cm. on average. Color on opening: center of bud, Orient pink, Red Group 36D, petals fading to white toward outside rows. Degree of pink color depends upon light intensity and temperature. Pink coloration is much more prevalent during cooler months.

*Flower.*—Shape: flat, slight recurve toward peduncle. Diameter: approximately 1.7 to 2.5 cm. on average. Color: center of bloom may retain some degree of Orient pink, Red Group 36D, depending upon weather conditions. The pink coloration is more prevalent during cooler periods. Color when fully open is usually pure white but often retains a pink blush as described above. Fragrance: none. Lasting quality: commonly several days. Texture: soft. Number of petals: approximately 40 to 50 on average, petals often retain adherence after turning brown. Stamens: not usually apparent. Pistils: approximately 40 to 50 on average, whitish with reddish top, organs are inconspicuous. Receptacle: light green, funnel shaped.

Development:

*Vegetation.*—Low, compact, vigorous and regular.

*Flowering.*—Very abundant throughout season.

*Fruit.*—Uncommon.

*Resistance to frost.*—Normal.

*Resistance to disease.*—Average.

I claim:

1. A new and distinct variety of Miniature rose plant, substantially as illustrated and described, wherein:

(a) from the physical standpoint the plant with light green adult wood has a low compact growth habit, and forms clusters of very double white flowers which often have a pink blush toward the center; and (b) from the biological standpoint the plant has vigorous and regular vegetation, and exhibits an abundant and repeated florescence throughout the growing season thereby creating a substantially constant floral display.

* * * * *